US012329692B2

(12) United States Patent
Elia

(10) Patent No.: US 12,329,692 B2
(45) Date of Patent: Jun. 17, 2025

(54) ROBOTIC HEAD HOLDING SYSTEM FOR SURGICAL PROCEDURES, AND ASSOCIATED DEVICES AND METHODS

(71) Applicant: Christopher Joseph Elia, Philadelphia, PA (US)

(72) Inventor: Christopher Joseph Elia, Philadelphia, PA (US)

( * ) Notice: Subject to any disclaimer, the term of this patent is extended or adjusted under 35 U.S.C. 154(b) by 478 days.

(21) Appl. No.: 17/181,951

(22) Filed: Feb. 22, 2021

(65) Prior Publication Data

US 2022/0265501 A1 Aug. 25, 2022

(51) Int. Cl.
*A61G 13/00* (2006.01)
*A61G 13/12* (2006.01)
*G08B 21/18* (2006.01)

(52) U.S. Cl.
CPC ....... *A61G 13/121* (2013.01); *A61G 13/0036* (2013.01); *A61G 13/0054* (2016.11); *A61G 13/129* (2013.01); *A61G 13/1295* (2013.01); *G08B 21/182* (2013.01); *A61G 2203/12* (2013.01); *A61G 2203/42* (2013.01); *A61G 2203/78* (2013.01)

(58) Field of Classification Search
CPC ......... A61B 90/14; A61B 90/50; A61B 90/57; A61B 34/30; A61B 34/70; A61B 34/76; A61H 1/02; A61H 1/0214; A61H 1/0218; A61H 1/0222; A61H 1/0229; A61G 7/07; A61G 13/121; A61G 13/1215; A61G 13/122; A61G 13/1255; A61G 13/129; A61G 13/1295; A61F 5/3707; A61F 5/3792; A61F 5/055; A61F 5/05891; A61F 5/05883

USPC .......................................................... 128/845
See application file for complete search history.

(56) References Cited

U.S. PATENT DOCUMENTS

| | | | | |
|---|---|---|---|---|
| 4,620,697 A | * | 11/1986 | Pithon | A61G 13/121 5/640 |
| 5,160,337 A | * | 11/1992 | Cosman | A61N 5/1049 378/209 |
| 10,548,798 B2 | * | 2/2020 | Hartman | A61H 1/0274 |
| 2006/0247557 A1 | * | 11/2006 | Coates | A61G 13/0054 600/595 |
| 2007/0282228 A1 | * | 12/2007 | Einav | A63B 21/00181 600/300 |
| 2014/0188129 A1 | * | 7/2014 | Kang | A61B 34/10 606/130 |
| 2016/0193098 A1 | * | 7/2016 | Nichols | A61G 13/121 602/32 |
| 2016/0213551 A1 | * | 7/2016 | Budagher | A61H 5/00 |
| 2017/0296838 A1 | * | 10/2017 | Asahina | A61G 15/125 |
| 2018/0049839 A1 | * | 2/2018 | Seong | B25J 9/1697 |

(Continued)

*Primary Examiner* — Adam Baker
(74) *Attorney, Agent, or Firm* — Perkins Coie LLP

(57) ABSTRACT

The present technology is directed to robotic systems that support and selectively adjust a position of a patient's head and neck during surgery. The robotic head holding systems may include a patient engagement assembly for supporting a portion of the patient and one or more arm segments connecting the patient engagement assembly to a surgical bed. An actuator can move the patient engagement assembly and/or the one or more arm segments to adjust a position of the patient, and a controller can receive user inputs for automatically controlling operation of the actuator.

10 Claims, 9 Drawing Sheets

(56) References Cited

U.S. PATENT DOCUMENTS

2019/0015685 A1\* 1/2019 Ostyn .................... A61G 13/02
2020/0229778 A1\* 7/2020 Bittner ............... A61G 13/1285

\* cited by examiner

ROBOTIC HEAD HOLDING SYSTEM FOR SURGICAL PROCEDURES, AND ASSOCIATED DEVICES AND METHODS

TECHNICAL FIELD

The present technology relates to robotic head holding systems for surgical procedures, such as cranial and spinal surgery.

BACKGROUND

Cranial and spinal surgery are used to treat a variety of pathological processes. During these procedures, patients are typically placed on a surgical table in a prone, supine, or other position. These tables generally include a head holder for supporting the patient's head while the patient is undergoing surgery. During certain procedures (e.g., cranial, cervical, and upper-thoracic procedures), the positioning of the head and neck region can impact the outcome of the surgery. The optimal position is dependent on the type of procedure being performed and can vary depending on the pathological process being treated. For example, for a posterior cervical decompression, the patient's neck should be slightly flexed to aid the decompression. For a posterior cervical fusion, the patient's neck should be neutral or under slight extension to achieve physiological cervical alignment. For certain complex cranial cases, the patient's head may need to be rotated, side bent, flexed, or extended to provide appropriate access to target surgical regions within the patient's brain. Of course, during surgery, a surgeon may need to adjust the positioning of the patient, such as if different surgical steps require different patient positions, if the original position of the patient is determined to be sub-optimal intra-operatively, to correct a spine deformity, to reduce a spinal fracture, or for any number of reasons. However, conventional head holding systems require the surgeon to manually manipulate the position of the patient's head and neck and/or break scrub to manipulate the position of the patient's head and neck. This can be risky to the patient for a number of reasons, especially if the brain or spinal cord are exposed and vulnerable. For example, the surgeon may manipulate the position of the head or neck into a non-physiological state. As another example, the duration of the surgical procedure may be increased due to the need for the surgeon to break scrub, which may lead to longer recovery times and a greater risk of infection. As a result of the foregoing, the surgeon may elect to perform the procedure in a suboptimal position, rather than adjusting the patient to the optimal position, which itself carries risks for the patient. Accordingly, a need exists for better surgical head holding systems that enable a surgeon to more easily adjust and stabilize the positioning of a patient's head and neck during cranial and spinal surgery.

DETAILED DESCRIPTION

I. Overview of Technology

Figure 1:
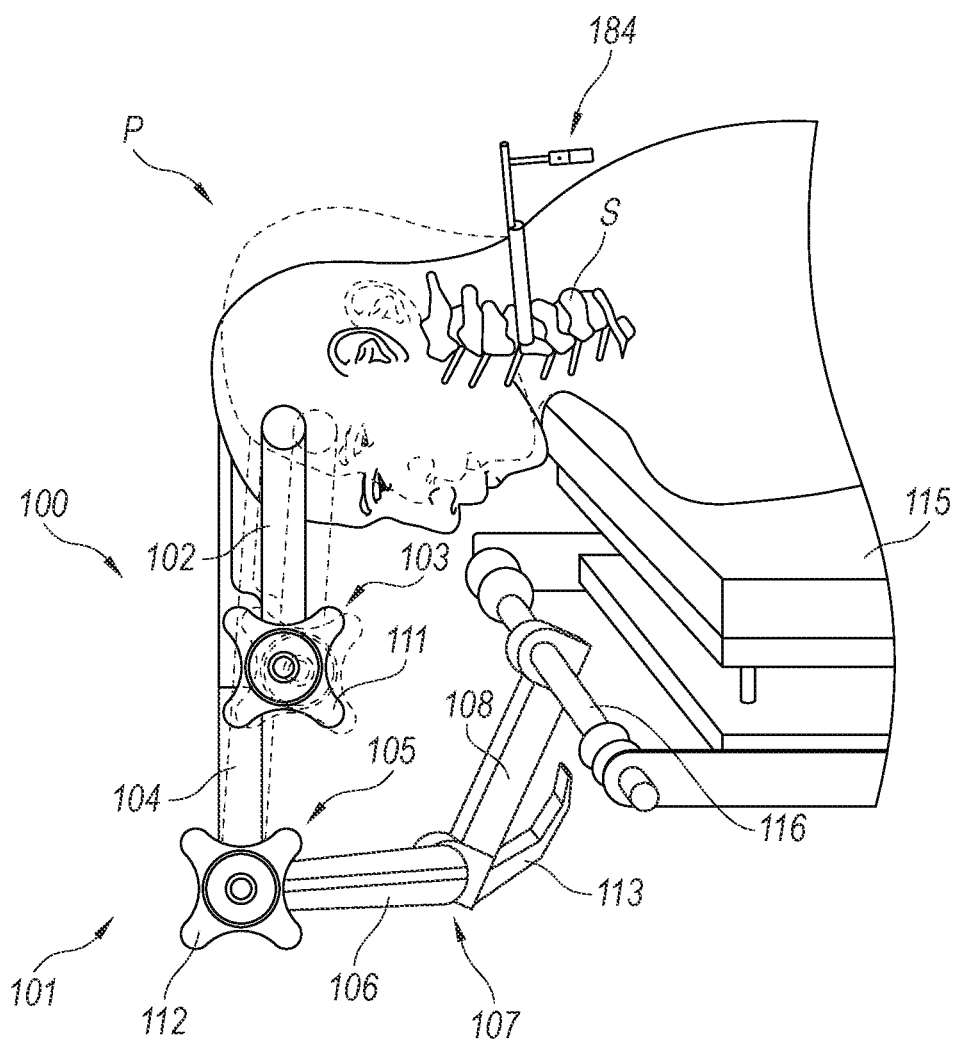
FIG. 1 illustrates an operative setup including a manually-adjustable head holding system with a patient in the prone position.

The present technology is directed to robotic systems and methods for supporting a patient during spine and cranial surgery. For example, in many of the embodiments described herein, the present technology includes robotic head holding systems that can support and selectively adjust a position of a patient's head and neck during surgery. The robotic head holding systems may include a patient engagement assembly (e.g., a head clamp) for supporting a portion of the patient and one or more arm segments connecting the patient engagement assembly to a surgical bed. The robotic head holding systems can further include an actuator that can move the patient engagement assembly and/or the one or more arm segments to adjust a position of the patient, and a controller for controlling operation of the actuator. In some embodiments, the controller is configured to receive a user input corresponding to a desired adjustment to the patient position, and, in response to the input, automatically direct the actuator to adjust a position of the patient engagement assembly and/or the one or more arm segments such that the position of the patient is adjusted in accordance with the desired positional adjustment.

In some embodiments, a robotic head holding system may include a head clamp for securely holding a patient's head during cranial or spinal surgery, and an arm assembly comprising one or more arm segments configured to couple the head clamp to an operating table. The arm assembly is robotically adjustable and can position the patient's head and/or neck at one or more user selected positions to facilitate performance of at least a portion of the surgical procedure. The robotic head holding system further includes a controller in communication with the arm assembly that is programmed to control movement of the arm assembly to keep the patient's head and/or neck at the user selected position and/or within a target range associated with the user selected position (e.g., ranges of motion, range of applied force, etc.). For example, the controller can be programmed to receive a user input corresponding to a desired adjustment to the patient position, and, in response to the input, automatically direct the arm assembly to position the patient's head and/or neck according to the desired positional adjustment.

In some embodiments, the robotic head holding systems further include a monitoring system that can provide safety and other alerts. The monitoring system may include sensors that measure one or more aspects about the system. For example, the sensors may be configured to measure a position and/or orientation of the patient engagement assembly and/or the one or more arm segments. The system (e.g., the controller or other computing device) can then calculate a position of the patient based on the measured position and/or orientation of the patient engagement assembly and/or the one or more arm segments. The system can generate an alert if the calculated position does not comply with one or more safety criteria (e.g., ranges of motion, etc.). Alternatively or additionally, the sensors can be configured to measure one or more metrics associated with a resistance to movement as the patient engagement assembly and/or the one or more arms are being adjusted. The system (e.g., the controller or other computing device) can compare the measured resistance to a predetermined resistance threshold, and, if the measured resistance exceeds the predetermined resistance threshold, generate an alert. The resistance can be based on force measurements, displacement measurements, pressure measurements, etc. For example, the patient's resistance to movement can be determined based on body part movement (e.g., displacement, rotation, etc.) and the force applied by the system.

II. Definitions

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

As used herein, the terms "connected," "coupled," or any variant thereof, means any connection or coupling, either direct or indirect, between two or more elements; the coupling of connection between the elements can be physical, logical, or a combination thereof.

As used herein, the words "herein," "above," "below," and words of similar import, when used in this application, shall refer to this application as a whole and not to any particular portions of this application.

As used herein, the phrase "and/or" as in "A and/or B" refers to A alone, B alone, and A and B.

Further, where specific integers are mentioned herein which have known equivalents in the art to which the embodiments relate, such known equivalents are deemed to be incorporated herein as if individually set forth.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. The term "substantially" or grammatical variations thereof refers to at least about 50%, for example, 75%, 85%, 95%, or 98%.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

III. Manually-Adjustable Head Holding Systems

FIG. 1 illustrates a manually-adjustable surgical head holding system 100 ("the system 100") for use with surgical procedures. The system 100 includes a head clamp or patient engagement assembly 102 (referred to herein as the "patient engagement assembly 102") for supporting the head of a patient P during a surgical procedure, such as a surgical procedure on the patient's spine S using a surgical tool 184. The system 100 further includes an arm assembly 101 coupling the patient engagement assembly 102 to a surgical bed 115. The arm assembly 103 can be reconfigured to move the head of the patient to a target position. The arm assembly 103 includes a first arm segment 104, a second arm segment 106, and a third arm segment 108 coupling the patient engagement assembly 102 to the surgical bed 115. The first arm segment 104 can extend between the patient engagement assembly 102 and the second arm segment 106, the second arm segment 106 can extend between the first arm segment 104 and the third arm segment 108, and the third arm segment 108 can extend between the second arm segment 106 and an adapter 116 configured to secure the system 100 to the surgical bed 115.

The patient engagement assembly 102, the first arm segment 104, the second arm segment 106, and the third arm segment 108 can be moveably coupled. For example, the patient engagement assembly 102 can be coupled to the first arm segment 104 at a first joint 103, the first arm segment 104 can be coupled to the second arm segment 106 at a second joint 105, and the second arm segment 106 can be coupled to the third arm segment 108 at a third joint 107. The first joint 103 can include a first locking mechanism 111 (e.g., mechanical knob, pin assembly, etc.) that can be manually loosened to unlock the first joint 103 (e.g., permitting the patient engagement assembly 102 to move relative to the first arm segment 104) and tightened to lock the joint (e.g., restricting movement of the patient engagement assembly 102 relative to the first arm segment 104). Likewise, the second joint 105 can include a second locking mechanism 112 for locking and unlocking the second joint 105, and the third joint 107 can include a third locking mechanism 113 for locking and unlocking the third joint 107.

To adjust a position of the patient engagement assembly 102 and/or the position of the patient P's head, a user (e.g., a surgeon) generally manually unlocks one or more of the locking mechanisms 111-113 and manually articulates the corresponding arm segments into an appropriate position. Once in the desired position, the user then generally manually locks the one or more locking mechanisms 111-113. For example, to move the patient P from a first position (shown in FIG. 1 in solid line) to a second position (shown in FIG. 1 in broken line), a user would loosen the second locking mechanism 112 and manually bend the first arm segment 104 relative to the second arm segment 106 about the second joint 105. The user would then tighten the second locking mechanism 112 to secure the patient P in the second position.

Requiring a user to manually adjust the position of the arm segments to adjust the position of the patient P is sub-optimal for several reasons. First, an operation may include multiple surgical steps that are best performed with different and/or complex patient head positions, requiring a surgeon or other user to adjust the position of the patient's head intra-operatively. As described above, to adjust the position of the patient P using the system 100, the surgeon or other user must unlock one or more of the joints and manually articulate the patient engagement assembly 102 into a desired position. This takes time and may require the surgeon to break scrub, further lengthening the duration of the surgery. Moreover, the adjustment may require two users: a first user to unlock the desired joint and a second user to stabilize and manipulate the patient's head into the desired position. Second, there are generally no feedback mechanisms to prevent the surgeon from placing the patient in a non-physiological position (e.g., flexing or extending the neck beyond physiological limits, rotating the head beyond physiological limits, etc.). This can lead to patient injuries and sub-optimal surgical outcomes. Third, a surgeon typically can only loosen one joint at a time, meaning the system 100 can only be adjusted about one joint at a time. This increases the time and complexity of adjusting the patient's head. Fourth, the joints may wear down over time and may not lock as well, increasing the risk of accidental slippage, which may lead to patient injury. As described below, the robotic head holding systems of the present technology are expected to mitigate, improve, and/or obviate some or all of the foregoing disadvantages of conventional manually-adjustable surgical head holding systems.

IV. Select Embodiments of Robotic Head Holding Systems

FIGS. 2A-2D illustrate a robotic head holding system 200 ("the system 200") configured in accordance with select embodiments of the present technology. The system 200 includes certain features generally similar to certain features of the system 100. However, relative to the system 100, the system 200 is remotely and/or robotically adjustable, thereby preventing a user form having to manually manipulate the positions of the arm segments to adjust a position of the user P.

Figure 2A:
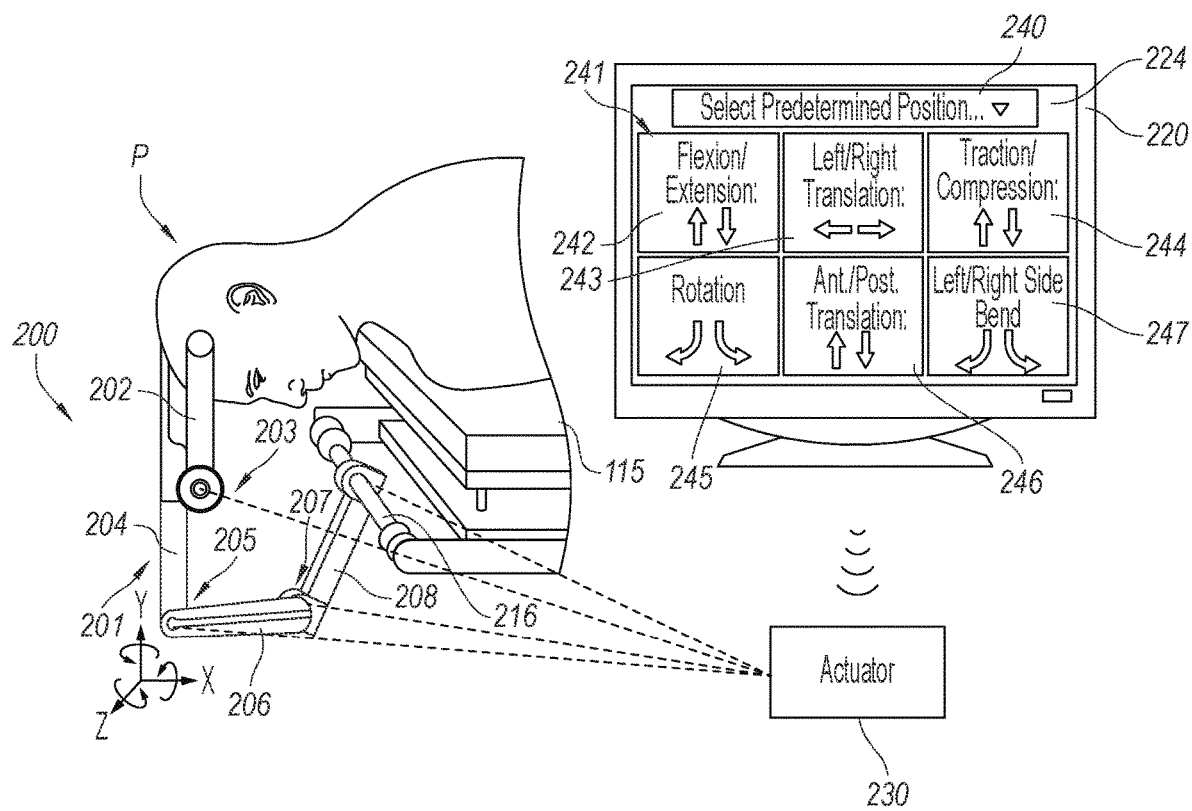
FIGS. 2A-2C illustrate an operative setup including a robotically adjustable head holding system configured in accordance with embodiments of the present technology.

Referring first to FIG. 2A, the system 200 includes a patient engagement assembly 202 for supporting the head of a patient P during a surgical procedure. The patient engagement assembly 202 can be any suitable component for supporting a patient's head, including, but not limited to, a head or skull clamp, a headrest, or the like. In some embodiments, the patient engagement assembly 202 is a multiple point head clamp (e.g., a two-point head clamp, a three-point head clamp, etc.) with disposable or reusable contact elements (e.g., pins) for securing the patient's head. The patient engagement assembly 202 can include a locking mechanism (not shown) for securing it to the arm assembly 201, described below.

The system 200 further includes an arm assembly 201 coupling the patient engagement assembly 202 to the surgical bed 115. The arm assembly 201 can include a first arm segment 204, a second arm segment 206, and a third arm segment 208. The first arm segment 204 can extend between the patient engagement assembly 202 and the second arm segment 206, the second arm segment 206 can extend between the first arm segment 204 and the third arm segment 208, and the third arm segment 208 can extend between the second arm segment 206 and an adapter 216 configured to secure the system 200 to the bed 115. The patient engagement assembly 202, the first arm segment 204, the second arm segment 206, and the third arm segment 208 can be moveably coupled. For example, the patient engagement assembly 202 can be moveably coupled to the first arm segment 204 at a first joint 203, the first arm segment 204 can be moveably coupled to the second arm segment 206 at a second joint 205, and the second arm segment 206 can be moveably coupled to the third arm segment 208 at a third joint 207.

The joints can be configured to enable each arm segment to have up to six degrees of freedom at the joint. For example, the joints may enable coupled arm segments to translate relative to one another, rotate relative to one another, or both translate and rotate relative to one another. Accordingly, the joints may permit the arm segments to move through one or more planes. For example, each joint (e.g., the first joint 203, the second joint 205, and the third joint 207) can permit rotation about and/or translation in the X direction, the Y direction, and/or the Z direction. In some embodiments, however, one or more of the joints may permit only one type of movement (e.g., translation or rotation) and/or movement about or in only one direction (e.g., the X direction, the Y direction, or the Z direction).

The system 200 can include an actuator 230 operably coupled to the patient engagement assembly 202, the first arm segment 204, the second arm segment 206, and the third arm segment 208. The actuator 230 can dynamically adjust the position of the patient engagement assembly 202 (and thus the patient's head, neck, and/or spine) by automatically moving the arm segments about the corresponding joints. For example, the actuator 230 can (i) move the patient engagement assembly 202 relative to the first arm segment 204 and/or move the first arm segment 204 relative to the patient engagement assembly 202 (e.g., about the first joint 203), (ii) move the first arm segment 204 relative to the second arm segment 206 and/or move the second arm segment 206 relative to the first arm segment 204 (e.g., about the second joint 205), and/or (iii) move the second arm segment 206 relative to the third arm segment 208 and/or move the third arm segment 208 relative to the second arm segment 206 (e.g., about the third joint 207). In some embodiments, the actuator 230 may drive more than one movement at a time. The movement can be of one or more types (e.g., translation, rotation, or both translation and rotation) and may occur in one or more directions (e.g., the X direction, the Y direction, or the Z direction).

The actuator 230 can be any suitable actuator for driving motion in the system 200. For example, in some embodiments the actuator 230 can be an electric motor, a stepper motor, a servo motor, a hydraulic motor, or the like. Although shown as a single actuator 230, in some embodiments the system 200 may include more than one actuator 230. For example, a first actuator may be positioned adjacent the first joint 203 for controlling movement thereat, a second actuator may be positioned adjacent the second joint 205 for controlling movement thereat, and a third actuator may be positioned adjacent the third joint 207 for controlling movement thereat.

The system 200 can further include a controller 220 for controlling operation of the actuator 230. The controller 220 can be a dedicated controller or other user device, such as a smart phone, a tablet, a laptop computer, a desktop computer, or other like. As illustrated, the controller 220 can include a display 224. In some embodiments, the display 224 can be a touchscreen configured to receive user input, although in other embodiments the controller 220 can include another input device (e.g., a remote control, a mouse, a keyboard, etc.) for providing user input to the controller.

A user can interact with the controller 220 to control the system 200. For example, in the illustrated embodiment, the controller 220 includes a drop-down menu 240 enabling a user to select from one or more predetermined positions for the patient P. As described in more detail below, to move the patient P to a specific predetermined position, a user (e.g., a surgeon) can select the specific predetermined position using the menu 240. Once selected, the controller 220 automatically directs the actuator 230 to manipulate the system 200 to achieve the specific predetermined position. As described in more detail below, the predetermined positions can include a starting position, a procedure-specific pre-set position, a patient-specific pre-set position, a specific maneuver position (e.g., traction, compression, etc.), or other predetermined positions.

In the illustrated embodiment, the controller 220 also includes an adjustment module 241 enabling a user to selectively and/or discretely adjust the position of the patient P. For example, the adjustment module 241 includes a flexion/extension positioner 242, a left/right translation positioner 243, a traction/compression positioner 244, a rotation positioner 245, an anterior/posterior translation positioner 246, and a left/right side bend positioner 247 (collectively referred to herein as the "positioners 242-247"). A user can adjust the position of the system 200 by interacting with the appropriate positioner. For example, to increase the flexion of the patient's neck, the user can press the "flexion" arrow in the flexion/extension positioner 242. To increase the extension of the patient's neck, the user can press the "extension" arrow in the flexion/extension positioner 242. As one skilled in the art will appreciate, the adjustment module 241 depicted in FIGS. 2A-2D is provided merely as a representative example, and in no way limits the present technology. Rather, the system 200 can include other adjustment modules 241 (e.g., including more or fewer positioners corresponding to the same or different motions) that a user can interact with to adjust the system 200.

In some embodiments, the display 224 on the controller 220 may provide a virtual rendering or image of a patient's head in its current position. The display 224 may also display a requested or potential change to the position/orientation of the patient's head, e.g., in response to a surgeon or other user selecting a predetermined position or otherwise interacting with the controller 220. In some embodiments, this can be done before adjusting the position of the patient so that the surgeon can virtually review the adjusted position of the patient before committing to the change in the patient position. After the movement, the display 224 may have a generated default image of what the general head/spine alignment should look like based upon the orientation of the robotic apparatus.

Figure 2B:
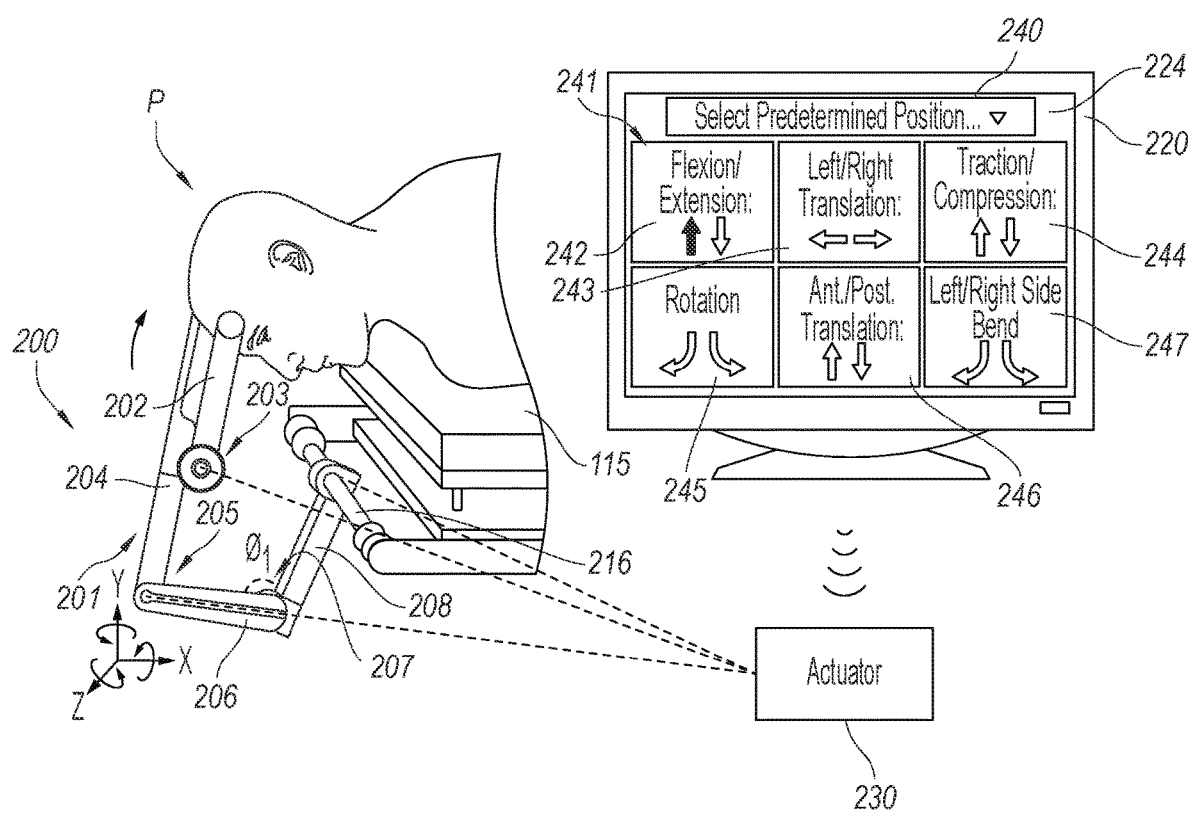

FIG. 2A illustrates the patient P in a neutral position. This may correspond to an initial or starting position of the patient P. FIG. 2B illustrates the patient P in a slightly extended position (e.g., cervical extension). To move the patient P from the neutral position shown in FIG. 2A to the extended position shown in FIG. 2B, a user can either select a predetermined position corresponding to the extended position from the menu 240 on the controller 220, or increase the extension using the "extension arrow" of the flexion/extension positioner 242 of the adjustment module 241. In either case, the controller 220 directs the actuator 230 to automatically adjust the patient engagement assembly 202 and/or one or more arm segments to direct the patient P into the extended position shown in FIG. 2B. This may be achieved, for example, by rotating the second arm segment 206 relative to the third arm segment 208 to decrease an angle $\theta_1$ defined between the second arm segment 206 and the third arm segment 208. Although shown as primarily moving at the third joint 207 for simplicity, movement may simultaneously occur at additional joints to position the patient P in the desired position. To return the patient P to the neutral position from the extended position, the user can select a predetermined position corresponding to the neutral position from the menu 240 on the controller 220, or reduce the extension using the "flexion arrow" of the flexion/extension positioner 242 of the adjustment module 241.

Figure 2C:
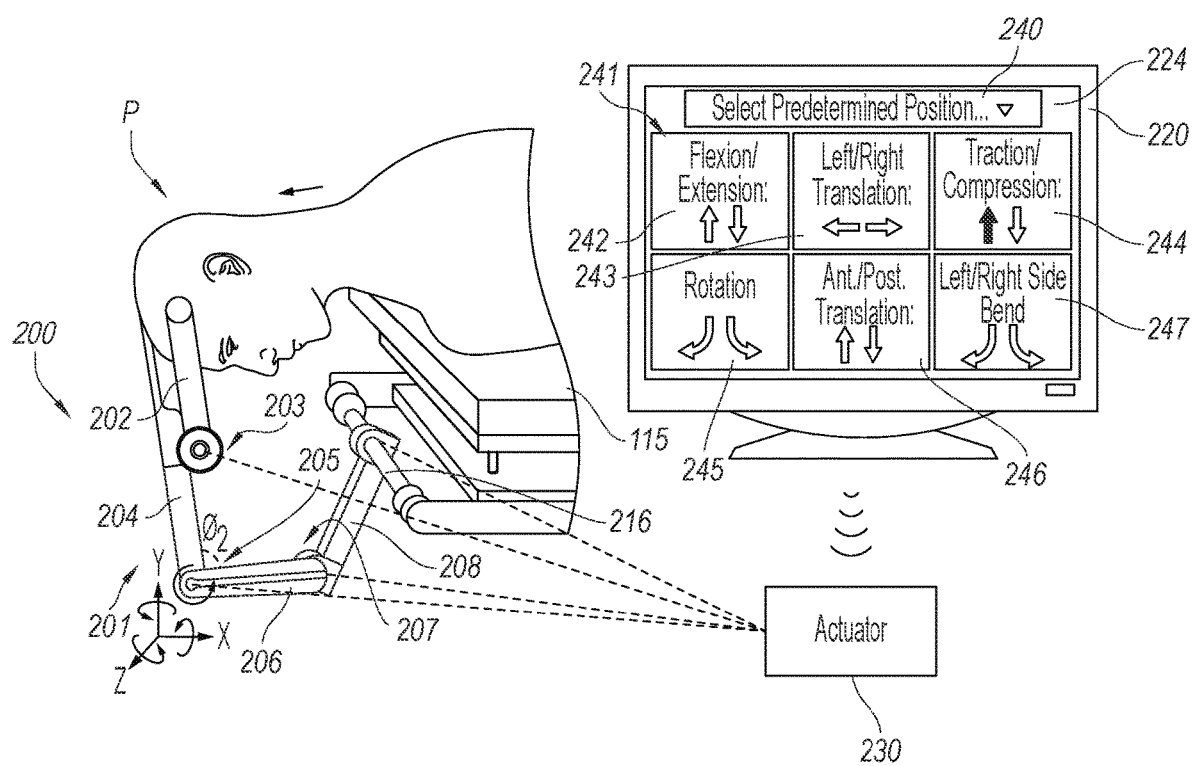

FIG. 2C illustrates the patient P under traction. To move the patient P from the neutral position shown in FIG. 2A to the traction position shown in FIG. 2C, a user can either select a predetermined position corresponding to the traction position from the menu 240, or can increase the traction using the "traction arrow" of the traction/compression positioner 244 of the adjustment module 241. In either case, the controller 220 directs the actuator 230 to automatically adjust the patient engagement assembly and/or one or more arm segments to direct the patient P into the traction position shown in FIG. 2C. This may be achieved, for example, by rotating the first arm segment 204 relative to the second arm segment 206 to increase an angle $\theta_2$ defined between the first arm segment 204 and the second arm segment 206. Although shown as primarily moving at the second joint 205 for simplicity, movement may simultaneously occur at additional joints to position the patient P in the desired position. In some embodiments, the display 241 or other monitor may show the amount of traction applied in pounds or other suitable metric to allow the user to assess the degree of traction applied. In some embodiments, the vector of traction/compression can also be adjusted to allow the user to apply traction/compression in a desired orientation to achieve one or more surgical goals (e.g. reducing a fracture, adjusting spinal alignment, etc.). To return the patient P to the neutral position from the traction position shown in FIG. 2C, the user can select a predetermined position corresponding to the neutral position from the menu 240 on the controller 220, or decrease the traction using the "compression arrow" of the traction/compression positioner 244 of the adjustment module 241.

Figure 2D:
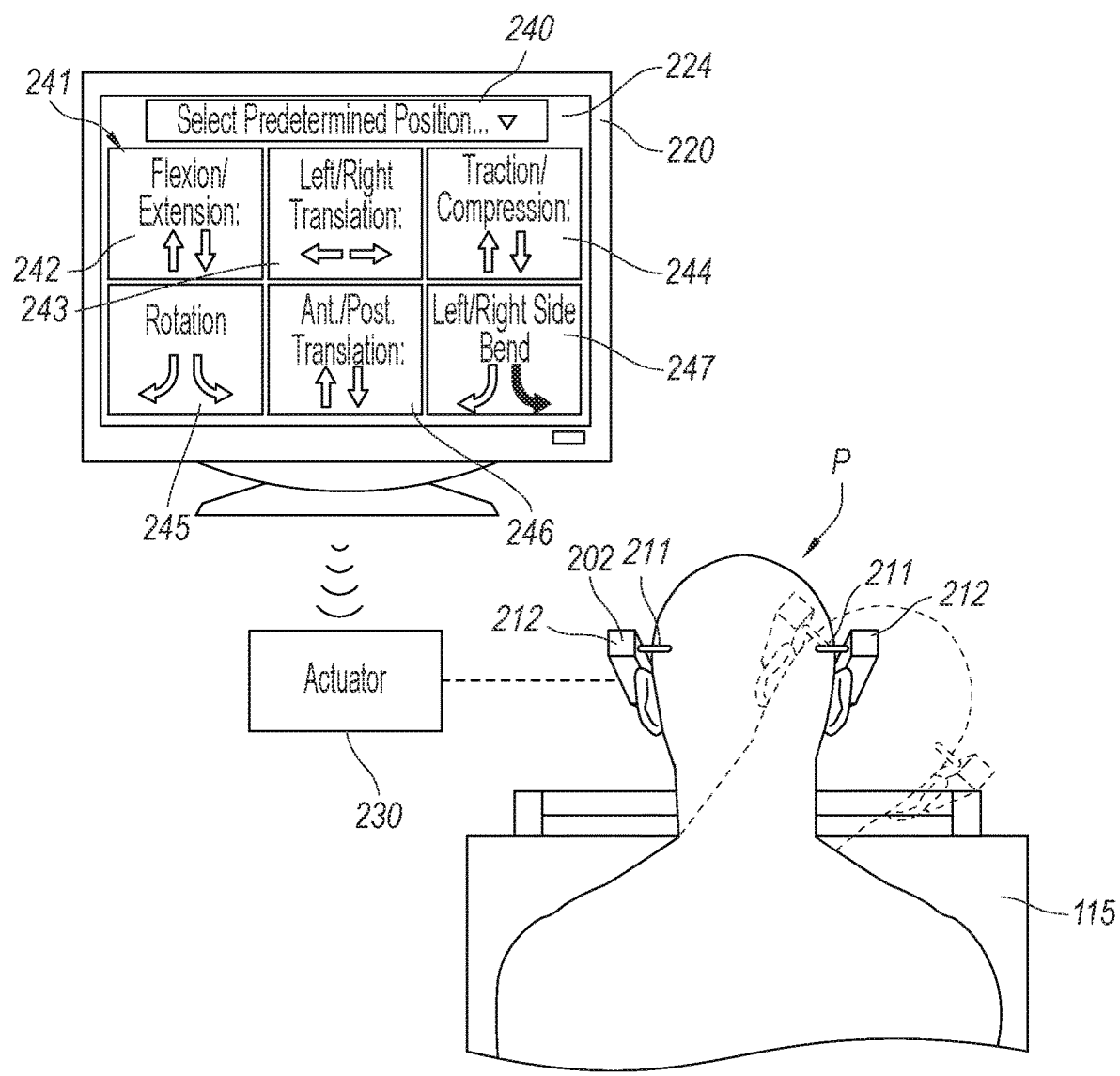
FIG. 2D is a top-down view of the operative setup shown in FIGS. 2A-2C.

FIG. 2D is a top down view of the patient P and the system 200 and illustrates moving the patient from the neutral position (shown in solid line) to a right side-bending position (shown in broken line). To move the patient P from the neutral position to the right side-bending position, a user can either select a predetermined position corresponding to the right-side bending position from the menu 240, or can increase the right side bend using the "right arrow" of the left/right side bend positioner 247 of the adjustment module 241. In either case, the controller 220 directs the actuator 230 to automatically adjust the patient engagement assembly and/or one or more arm segments to direct the patient P into the right side-bending position. This may be achieved, for example, by rotating the patient engagement assembly 202 relative to the first arm segment 204. To return the patient P to the neutral position from the right side-bending position, the user can select a predetermined position corresponding to the neutral position from the menu 240 on the controller 220, or decrease the right side-bend using the "left arrow" of the left/right side bend positioner 247 of the adjustment module 241.

FIG. 2D also illustrates additional aspects of the patient engagement assembly 202. For example, as shown in FIG. 2D, the patient engagement assembly 202 can be a head clamp having contact elements 211, such as pins (e.g., axial pins, rocker pins, etc.), pads, etc. The patient engagement assembly 202 further includes clamp arms 212 connected to the contact elements 211 and configured to extend at least partially around the patient's head. When the patient engagement assembly 202 is in an open configuration, the patient's head can be between, but not secured to, the contact elements 211. The patient engagement assembly 202 can be moved to a closed configuration such that the contact elements 211 apply a desired clamping force to the head. The patient engagement assembly 202 can monitor the clamping force when the head is moved and/or stationary. In some embodiments, the clamping force applied by the patient engagement assembly 202 can be increased or decreased when the head is repositioned to inhibit or prevent trauma to the skull and/or to prevent slippage. In some embodiments, the system 200 can monitor the clamping force during surgery to detect adverse events, such as improper patient position, tissue swelling, excessively high surgeon applied forces, or the like.

As one skilled in the art will appreciate, the positions and adjustments shown in FIGS. 2A-2D are provided merely as representative examples of the patient positioning that can be achieved using the system 200. The system 200 can direct the patient into positions other than those expressly illustrated herein, and is in no way limited to the positions described and shown herein. For example, the system 200 can manipulate a patient to achieve various degrees of rotation, flexion, extension, traction, compression, axial loading, translation, side-bending, and the like.

The system 200 is configured to be "self-braking" and thus does not necessarily include the manually adjustable locking mechanisms of the system 100 (e.g., the mechanical knobs 111-113 shown in FIG. 1). For example, the system 200 can be self-braking such that, following actuation, the system 200 automatically retains its actuated position. In some embodiments, the system 200 can be configured such that all joints are "locked" unless being actively actuated. This helps maintain adjusted patient positions and ensure patient safety. Optionally, the system 200 may have an "unlock all" feature that can be selected on the controller 220 or otherwise applied to the system 200 that unlocks all of the joints and permits the system 200 to be manually manipulated by a user (e.g., to manually adjust the patient's head/neck position if desired or to reduce the profile of the system 200 for storage). If the user manually adjusts the position, they can lock the joints in place once the desired position is achieved. This can be done by a remote locking option or by the surgeon releasing an "unlock" trigger/button. Of course, in some embodiments the system 200 can optionally further include a manual locking mechanism (e.g., similar to the mechanical knobs 111-113) to permit a user to manually adjust the position of the system 200, if desired.

In some embodiments, the patient engagement assembly 202, the first arm segment 204, the second arm segment 206, and the third arm segment 208 can be a single integral piece. In other embodiments, the patient engagement assembly 202, the first arm segment 204, the second arm segment 206, and the third arm segment 208 are distinct components coupled together at their respective end regions. Moreover, although described as having three arm segments and three joints, the system 200 can have more or fewer arm segments and joints, such as one, two, three, four, five, six, seven, eight, or more.

As provided above, the system 200 can be coupled to a surgical bed 115 via the adapter 216. Although illustrated as a conventional surgical bed 115, the system 200 can also be coupled to other types of beds, such as a Jackson table, to increase the versatility of the system. To do so, the system 200 may be used with an adapter suitable for connection with the Jackson bed. In some embodiments, the system 200 may be configured for use with other surgical tools, such as navigation systems.

The system 200 may also include additional features not expressly illustrated in FIGS. 2A-2D. For example, the system 200 may include one or more internal batteries for powering the controller 220 and/or the actuator 230. Alternatively or additionally, the system 200 may include one or more power cords for plugging the system 200 into a standard electrical power outlet for charging the one or more internal batteries and/or for directly powering the controller 220 and/or the actuator. The system 200 can further include a monitoring system, described in detail below with respect to FIG. 4.

Figure 3:
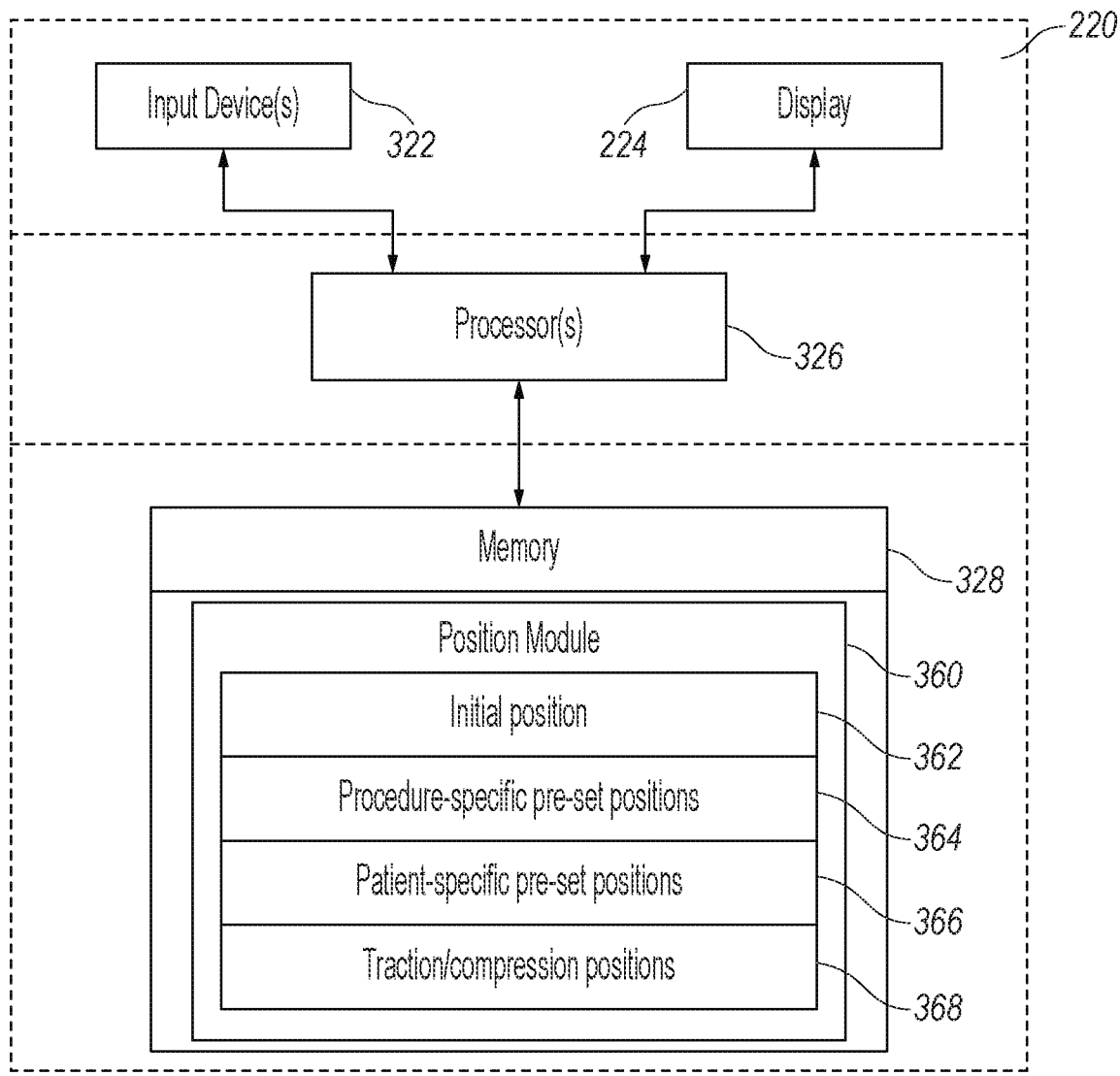
FIG. 3 is a schematic illustration of a controller of the robotically adjustable head holding system of FIGS. 2A-2D and configured in accordance with select embodiments of the present technology.

FIG. 3 is schematic illustration of the controller 220 shown in FIGS. 2A-2D. As illustrated, the controller 220 includes one or more input devices 322 for receiving user input. The input devices 322 can include a remote control, a touchscreen, a touchpad, a mouse, a keyboard, a joystick, or other suitable input devices. The input device 322 enables a user to interact with the controller 220 and the system 200. For example, in embodiments in which the input device 322 is a remote control, the input device 322 may include physical buttons corresponding to the positioners 242-247 of the adjustment module 241 (FIGS. 2A-2D) that permit a user to selectively adjust the position of the patient P by interacting with the remote. A user may also be able to toggle between different display interfaces via the input device 322. In some embodiments, the input device 322 is sterilized and/or draped to prevent a surgeon from having to break scrub while interacting with the input device 322.

As previously described with respect to FIGS. 2A-2D, the controller 220 further includes a display 224. The display 224 can be a touchscreen, an LCD display screen, an LED display screen, a projected, holographic, or augmented reality display, or the like. In some embodiments (e.g., as described with respect to FIGS. 2A-2D), the display 224 and the user input device 322 can be the same component (e.g., a touchscreen). Accordingly, in some embodiments the display 224 is configured to display user controls (e.g., the menu 240 and the adjustment module 241) to the user. The display 224 can also display other system metrics to the user. For example, the display 224 can include one or more virtual models corresponding to the operative procedure, such as a virtual model of the patient P and the system, and/or a virtual model of select patient anatomical structures (e.g., to show flexion of the patient's cervical vertebrae when in the flexed position, etc.). The display 224 may further display other aspects of a surgical plan. The display 224 may also provide system metrics associated with a monitoring system (described below with respect to FIG. 4), battery-life information, or the like.

The controller 220 further includes one or more processors 326 and a memory 328. The processor(s) 326 (which can be a CPU(s), GPU(s), HPU(s), etc.) can be a single processing unit or multiple processing units in a device or distrusted across multiple devices. The processor(s) 326 can be coupled to other hardware devices, for example, with the use of a bus, such as a PCI bus or SCSI bus. The processor(s) 326 can be configured to execute one or more computer-readable program instructions, such as program instructions to carry out any of the operations and methods described herein.

The memory 328 can be a non-transitory memory storing various software modules and instructions for performing one or more steps of the operations and methods described herein. For example, the memory 328 can include a position module 360. The position module 360 can store surgical plans and/or predetermined patient positions (e.g., that may be available via the menu 240), such as an initial position 362 (e.g., corresponding to the neutral position shown in FIG. 2A), one or more procedure-specific pre-set positions 364, one or more patient-specific pre-set positions 366, one or more traction/compression positions 368, and the like.

The position module 360 can include computer-executable instructions corresponding to each position 362-368. In response to receiving a user input (e.g., via the input device 322) selecting a specific predetermined position, the processor 326 can retrieve and execute the computer-executable instructions corresponding to the selected position. As the controller 220 executes the instructions, it directs the actuator 230 to manipulate the patient engagement assembly and/or the one or more arm segments to achieve the selected position. In some embodiments, a user (e.g., a surgeon) can set and/or select the predetermined patient positions that will be available for a specific operation before performing the operation. For example, a surgeon may prefer to have the patient in flexion when performing a decompression and instrumentation of the cervical spine and then in extension when placing a rod. Accordingly, the surgeon can preset a flexion position for the decompression and instrumentation steps and an extension position for placing the rod.

Figure 4:
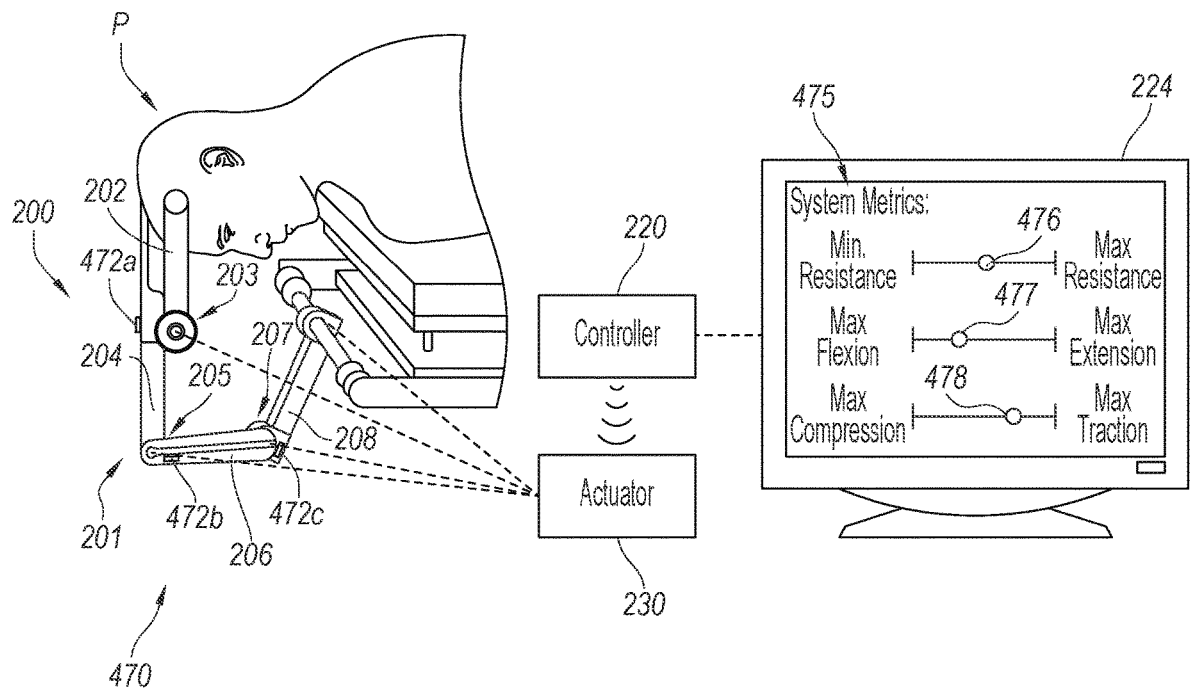
FIG. 4 is a partially schematic view of an operative setup including a monitoring system for use with the robotically adjustable head holding system of FIGS. 2A-2D and configured in accordance with embodiments of the present technology.

FIG. 4 illustrates the system 200 with a monitoring system 470 configured in accordance with select embodiments of the present technology. The monitoring system 470 includes one or more sensors 472 for monitoring one or more system metrics. For example, the monitoring system 470 includes a first sensor 472a positioned proximate the first joint 203, a second sensor 472b positioned proximate the second joint 205, and a third sensor 472c positioned proximate the third joint 207. Although shown as having three sensors 472, the monitoring system 470 may have more or fewer sensors, such as one, two, four, five, six, seven, eight, or more.

As provided above, the sensors 472 are configured to measure one or more system metrics. For example, the sensors 472 can be position sensors configured to measure a spatial position or orientation of the patient engagement assembly 202, the first arm segment 204, the second arm segment 206, and/or the third arm segment 208. In such embodiments, the sensors 472 may measure metrics associated with a distance and orientation of the sensors 472 relative to a reference position. The sensors 472 can transmit the measured metrics to the controller 220 or other computing device, which can then calculate the position of the patient engagement assembly 202, the first arm segment 204, the second arm segment 206, and/or the third arm segment 208 based on the measured metrics. The controller 220 or other computing device can then calculate the position of the patient P based on the calculated position of the patient engagement assembly 202, the first arm segment 204, the second arm segment 206, and/or the third arm segment 208.

Alternatively or additionally, the sensors 472 can be configured to measure one or more metrics (e.g., pressures, forces, torques, displacements, etc.) corresponding to or otherwise indicative of a pressure at the patient and/or a resistance to movement imparted by the patient's physiology when the actuator 230 is adjusting a position of the patient engagement assembly 202 and/or the arm assembly 201. The sensors 472 can transmit the metrics to the controller 220 or other computing device. Further yet, one or more of the sensors 472 can include an accelerometer for measuring the speed of movement in the system 200. In such embodiments, the one or more sensors 472 can direct the controller 220 to automatically lock the system 200 if the one or more sensors 472 detect abrupt motion that may indicate a slippage or other adverse event.

The monitoring system 470 can compare the measured system metrics to associated criteria (e.g., adverse event criteria, safety criteria, target position criteria, etc.). For example, if the sensors 472 are configured to measure position metrics, the monitoring system 470 may calculate a position of the patient P from the measured position metrics and compare the calculated patient P position to a maximum acceptable range of motion. The maximum acceptable range of motion may include specific values corresponding to certain movements (e.g., maximum flexion of 80 degrees, maximum extension of 70 degrees, maximum right side-bending of 40 degrees, maximum left side-bending of 40 degrees, maximum left-rotation of 80 degrees, maximum right-rotation of 80 degrees, etc.). In some embodiments, the monitoring system 470 can generate an alert (e.g., an audio alarm, a visual alert, etc.) if the calculated position exceeds one or more of the safety criteria. For example, if the safety criteria includes a maximum flexion of 80 degrees, the monitoring system 470 may generate an alarm if the surgeon adjusts the system 200 such that the patient P has a flexion of 85 degrees. The alarm can provide a warning to the surgeon that the patient P is in a non-physiological or otherwise unsafe position. In some embodiments, the monitoring system 470 can provide a first alert if the measured data approaches one or more of the safety criteria thresholds (e.g., if the maximum flexion is 80 degrees and the calculated patient P flexion is 75 degrees), and a second alert different than the first alert if the measured data exceeds the safety criteria threshold (e.g., if the calculated patient P flexion is 85 degrees). In some embodiments, the monitoring system 470 prevents the surgeon from adjusting the position of the patient P to a position that does not comply with the safety criteria (e.g., the surgeon cannot manipulate the system to achieve a flexion of 85 degrees). In some embodiments, the surgeon may be able to override these restrictions, for example, in surgical operations requiring unusual positioning (e.g. severe spinal deformity). In embodiments in which the sensors 472 are configured to measure patient pressure and/or physiological resistance to movement, the monitoring system 470 can compare the measured metrics to one or more safety criteria associated with resistance (e.g., maximum acceptable resistance). If the measured metrics approaches or exceeds the maximum acceptable value, the monitoring system 470 can generate an alert indicating that the patient P is about to enter, or is in, a non-physiological or otherwise unsafe position.

In some embodiments, the user can select the adverse event criteria, safety criteria and/or alarm setting before performing a surgical operation on the patient. For example, the surgeon may input specific values corresponding to a maximum acceptable range of pressure, force, and/or motion for the specific patient (e.g., maximum flexion of 37 degrees, maximum extension of 26 degrees, maximum right-side bending of 35 degrees, etc.). The surgeon may also select whether they would like to receive a warning (e.g., a first alert) if they approach the safety criteria threshold, in addition to receiving an alert (e.g., a second alert) if they exceed the safety criteria threshold. The surgeon may also specify at what point the warning alert is generated (e.g., if the position of the patient is within 5 degrees, 10 degrees, or 15 degrees of a safety criteria threshold, etc.). In some embodiments, the monitoring system 470 can detect an adverse event or violation of one or more safety criteria, and direct the controller 220 to automatically perform a corrective action based on the event. The corrective action can be stopping movement of the patient, repositioning the patient to comply with the one or more safety criteria, or the like.

The monitoring system 470 can also provide a visual display of the measured system metrics. For example, in the illustrated embodiment, one or more system metrics 475 are displayed via the display 224 of the controller 220. The displayed system metrics 475 include resistance, flexion/extension, and compression/traction, although other metrics can be displayed in other embodiments. The metrics 475 can be displayed as a sliding scale to indicate how close the metrics 475 are to exceeding one or more safety criteria. For example, a first indicator 476 can indicate how close the measured resistance is to a maximum resistance. Likewise, a second indicator 477 can indicate where the calculated patient P position falls within an acceptable range between maximum flexion and maximum extension, and a third indicator 478 can indicate where the calculated patient P position falls within an acceptable range between maximum compression and maximum traction. Of course, other metrics can be displayed, including rotation, side-bending, or the like. In some embodiments, a user can specify which metrics are displayed.

In some embodiments, the monitoring system 470 may also track and/or display metrics associated with a current position of the patient P relative to a baseline. The baseline can be a starting or neutral position of the patient (e.g., a "zeroed" position). The system 470 can track how far the patient P is relative to the baseline. For example, if the baseline position included a flexion of 0 degrees, and the current patient position includes a flexion of 10 degrees, the system 470 can indicate the user has added 10 degrees of flexion relative to the baseline position. Tracking and displaying positional metrics relative to a baseline may help a user more quickly determine the current position of the patient P relative to a neutral or starting position. Likewise, the monitoring system 470 may track and/or display metrics associated with a resistance relative to baseline resistance forces. This also permits the user to monitor changes in resistance forces throughout the procedure.

The monitoring system 470 may include a separate dedicated computing device (not shown) for performing the calculations described above. However, in some embodiments, the memory 328 of the controller 220 can include a monitoring system module storing instructions for performing the calculations described above. In some embodiments, the display 224 of the controller 220 may display the system metrics 475. In other embodiments, the monitoring system 470 may include a separate dedicated display. In some embodiments, the display 224 may display the system metrics 475 simultaneous with the menu 240 (FIGS. 2A-2D) and the adjustment module 241 (FIGS. 2A-2D). In other embodiments, a user may selectively toggle between a first display screen showing the menu 240 and the adjustment module 241, and a second display screen showing the system metrics 475.

Figure 5:
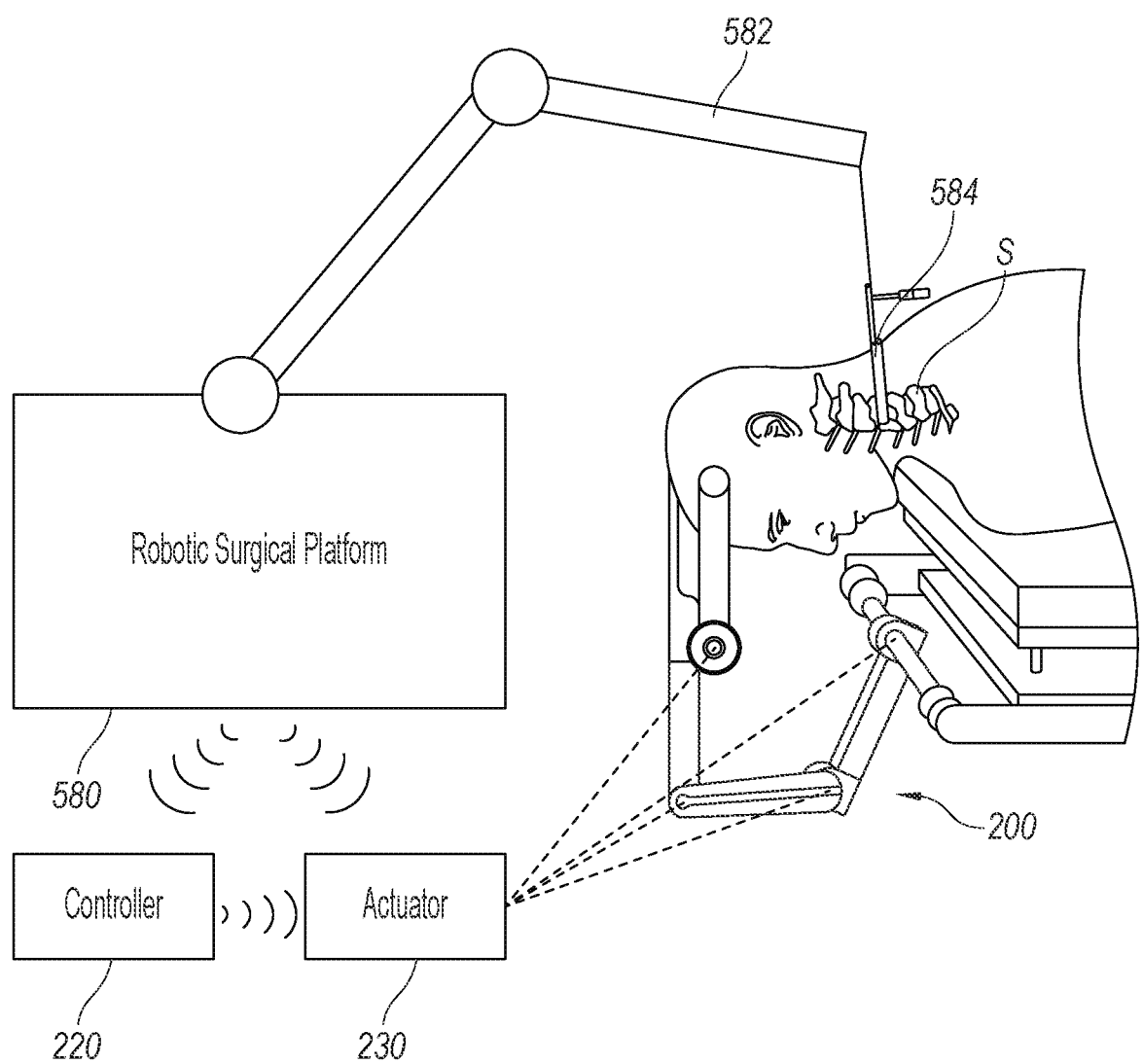
FIG. 5 is a partially schematic view of an operative setup including a robotic surgical platform for use with the robotically adjustable head holding system of FIGS. 2A-2D and configured in accordance with embodiments of the present technology.

FIG. 5 illustrates the system 200 being used with a robotic surgical platform 580 ("the platform 580") to perform an operative procedure in accordance with select embodiments of the present technology. In the illustrated embodiment, for example, the platform 580 is shown as performing a surgical procedure on the patient's cervical region of their spine S. As described below, the platform 580 can work in conjunction with the system 200 to automate (e.g., fully automate, partially automate, etc.) the surgical procedure.

The platform 580 can be any suitable robotic surgical platform, and may be configured to perform or otherwise assist with one or more aspects of the operative procedure, including, for example, navigation, selecting tissue incision sites, selecting implant delivery paths and trajectories, preparing tissue for an incision, making an incision, making a resection, removing tissue, manipulating tissue, performing a corrective maneuver, delivering an implant to a target site, deploying the implant at the target site, adjusting the implant at the target site, manipulating the implant once it is implanted, securing the implant at the target site, explanting the implant, suturing tissue, or the like. The platform 580 can include one or more arms 582 and end effectors 584 for holding various surgical tools (e.g., graspers, clips, needles, needle drivers, irrigation tools, suction tools, staplers, screw driver assemblies, etc.), imaging instruments (e.g., cameras, sensors, etc.), and/or medical devices and that enable the platform 580 to perform the one or more aspects of the surgical plan (e.g., positioning cages, forming mechanical connections, installing positioning features, implanting plates, etc.). Although shown as having one arm 582, one skilled in the art will appreciate that the platform 580 can have a plurality of arms (e.g., two, three, four, or more) and any number of joints, linkages, motors, and degrees of freedom. In some embodiments, the platform 580 may have a first arm dedicated to holding one or more imaging instruments, while the remainder of the arms hold various surgical tools. In some embodiments, the tools can be releasably secured to the arms such that they can be selectively interchanged before, during, or after an operative procedure. The arms can be moveable through a variety of ranges of motion (e.g., degrees of freedom) to provide adequate dexterity for performing various aspects of the operative procedure.

In some embodiments, the controller 220 is programmed with instructions that are associated with desired positions of the patient for various steps of a surgical plan being carried out by the platform 580. The platform 580 can communicate with the controller 220 and/or the actuator 230 to control the system 200. For example, rather than relying on a user input to initiate an adjustment to the position of the patient P, the platform 580 may automatically direct the controller 220 and/or the actuator 230 to adjust a position of the patient P. This may be done, for example, to synchronize the various operative steps performed by the platform 580 with the appropriate patient positioning to perform the operative steps. In some embodiments, the controller 220 commands the system 200 to move the patient's body part to target positions for performing respective operative steps. In some procedures, the controller 220 commands the system to move the patient's body part while performing the surgical procedure. The coordinate tool and body part movement enables a complex surgical procedure to be performed.

In some embodiments, the surgical plan can be modified based on data obtained during a procedure. For example, in some embodiments, the controller 220 and/or the platform 582 can be in communication with a visualization system (e.g., machine vision system, fluoroscopy system, etc.) configured to monitor position of the tool(s) and patient's body. The controller 220 and/or the platform 582 can be programmed to analyze image data from the visualization system. The controller 220 can periodically or continuously position the patient based the analysis. In some procedures, for example, the controller 220 is programmed to automatically move the position of the patient when a surgical step has been completed, e.g., as determined by the visualization system.

In some embodiments, the system 200 can be used in conjunction with surgical navigation systems during robotic assisted surgery. For example, the system 200 may have one or more attachment arms for a reference frame (not shown) of a surgical navigation system. During the digital planning of a surgery (e.g., a cervical or cervicothoracic spine deformity surgery), the surgeon can input the desired amount of spinal correction needed after the bony decompression and osteotomies are performed and the system 200 and/or the platform 580 may compute the change in head/neck position needed to acquire the deformity correction. The system 200 and/or the platform 580 may also suggest a change in position to achieve the desired alignment. The recommendations provided by the system 200 and the platform 580 can be accepted, declined or modified by the surgeon. If accepted by the surgeon, the system 200 may automatically adjust the patient's head/neck to the desired alignment prior to completion of the spinal fusion. If rejected by the surgeon, the system 200 and the platform 580 can provide a different recommendation, and/or the surgeon can adjust the position of the patient using the controller 220 (e.g., using the positioners 241-247 shown in FIGS. 2A-2D). The surgeon can also abort the change in position during the process, if desired.

V. Additional Aspects of the Present Technology

Figure 6:
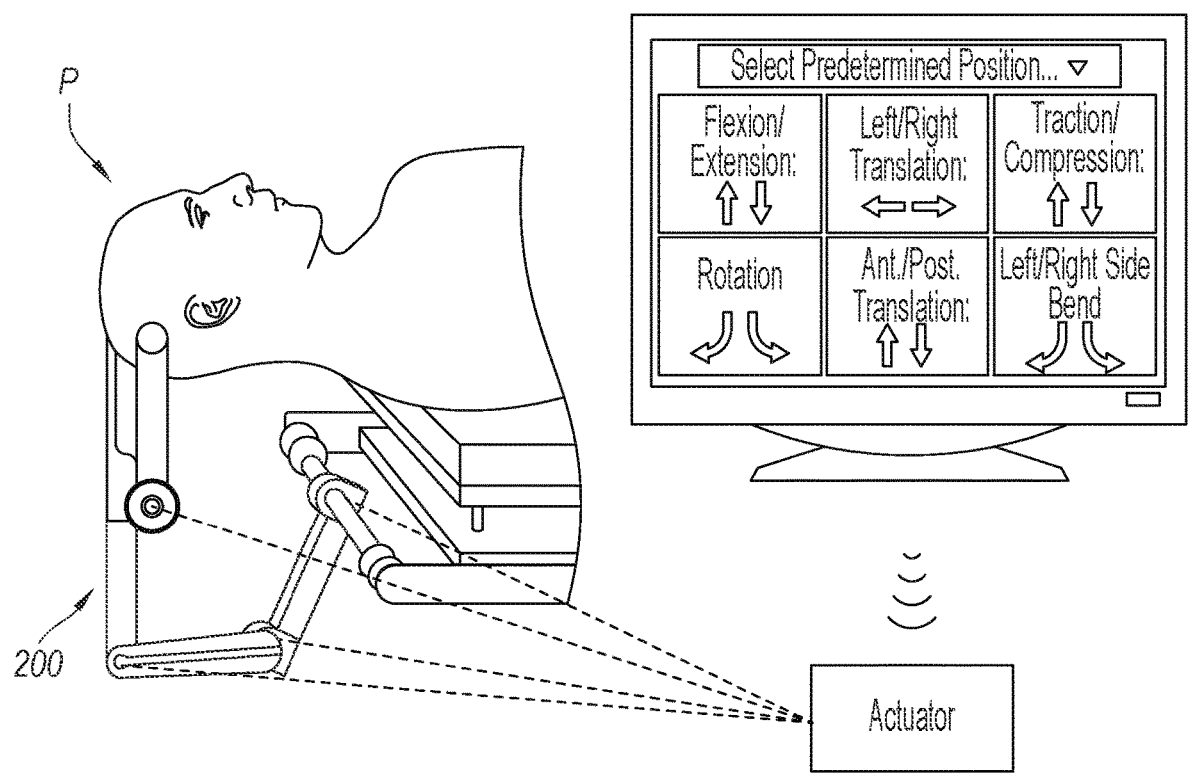
FIG. 6 illustrates the operative setup shown in FIGS. 2A-2C with a patient in a supine position in accordance with select embodiments of the present technology.

Without being bound by theory, the present technology can be utilized for a variety of surgical procedures, including, but not limited to, surgery at the brain, skull, skull base, occipitocervical junction, upper cervical spine, cervical spine, and thoracic spine. The surgery can include fusion spinal surgeries (e.g., anterior or posterior cervical fusion, cervicothoracic fusion, etc.), non-fusion spinal surgeries (e.g., cervical decompression), fracture repair (e.g., cervical and thoracic fractures/injuries, atlanto-occipital injuries), brain surgery (e.g., lesion biopsy/resection), or the like. Of course, the present technology can be used to perform other surgical procedures not expressly identified herein, and is therefore in no way limited to the procedures identified herein. In fact, one expected advantage of the present technology is its versatility and adaptability, which enables it to function for a variety of surgical procedures and for a variety of patient positions (e.g., prone, three-quarters prone, lateral, supine). FIG. 6, for example, illustrates an operative setup including the system 200 supporting a patient in a supine position, e.g., as commonly used for cranial surgeries. The present technology can also be used with a variety of operative beds (e.g., standard operative beds, Jackson beds, etc.), further increasing its versatility.

As a particular non-limiting example, the system 200 can be used in connection with an operative procedure to correct a cervical or thoracic deformity. Correcting a cervical deformity generally requires performing an osteotomy with the patient in a first position, then moving the patient to a second position to achieve a desired correction of the deformity before placing rods. Using a conventional manually-adjustable head holding system, a surgeon assistant must go under the sterile drapes and unlock the head-holding apparatus joints while the surgeon or another assistant grabs the skull clamp over the sterile drapes and manipulates the neck to the presumably desired position. All the joints must then be manually locked back into place under the sterile drapes by the assistant while the other surgeon/assistant continues to hold the head in the desired alignment. Once everything is locked into place an x-ray is usually obtained to confirm the appropriate/desired alignment is achieved. This process may be repeated multiple times if the alignment on x ray is not satisfactory. Using the present technology, however, a user (e.g., the surgeon) can quickly manipulate the patient to the second position to achieve the desired correction by selecting a predetermined position associated with the second position, and/or using the adjustment module 241 (FIGS. 2A-2D) to direct the patient to occupy the second position. In addition, the surgeon does not need to grab the skull clamp over the sterile drapes, which can risk contamination of the surgical field and wound. A similar process is also used in surgery of the upper cervical spine (atlas and axis/C1 & C2) and in fracture reduction.

As another non-limiting example, the system 200 can be used to apply traction. Traction is often required during surgical procedures to correct cervical and thoracic fractures and dislocations. For example, in the setting of spinal trauma, a surgeon may need to apply traction to a patient's head to reduce a fracture. However, manually-adjustable head holding systems cannot perform traction. Rather, a separate traction system (e.g., pully apparatus) must be used to apply traction. For example, traction is typically achieved by grasping the patient's head with Gardner-Wells tongs, and connecting weights hanging off the side of the operative bed to the Gardner-Wells tongs via rope. The tongs, although they can be used for traction, cannot hold the head in a fixed position like a typical skull clamp, nor can they be used to safely manipulate the patient's head/neck/spine into various orientations, such as flexion, extension, side bending, translation, rotation, etc. In addition, the tongs cannot be used to apply compressive forces, if needed. In contrast, the system 200 is capable of providing traction without the need for tongs and weights in addition to axial compression. Moreover, the amount of traction or compression applied can be measured in a more controlled fashion. Further yet, unlike Gardner-Wells tongs which can only apply traction in one vector, the system 200 can apply traction/axial compression in a multitude of different vectors which can be tailored to the patient's specific needs.

CONCLUSION

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

As one of skill in the art will appreciate from the disclosure herein, various components of the systems described above can be omitted without deviating from the scope of the present technology. Likewise, additional components not explicitly described above may be added to the systems without deviating from the scope of the present technology. For example, it will be appreciated that specific embodiments of the technology have been described herein for purposes of illustration, but well-known structures and functions have not been shown or described in detail to avoid unnecessarily obscuring the description of the embodiments of the technology. Moreover, although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. Accordingly, the present technology is not limited to the configurations expressly identified herein, but rather encompasses variations and alterations of the described systems and methods.

Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A computer-implemented method for adjusting a position of a patient during a cranial or cervical surgical procedure using a robotic head holding system, the method including:
   receiving, from a user, a request to adjust an intra-surgical position of the patient, wherein the adjustment includes at least one of increasing cervical flexion, increasing cervical extension, increasing cervical traction, or increasing cervical compression;
   in response to the request, automatically directing an actuator to adjust the intra-surgical position of the patient by adjusting a position of a patient engagement assembly fixedly secured to the patient's head;
   during and/or after adjusting the patient, receiving one or more measured intra-operative force-based metrics associated with the intra-surgical position of the patient and an intra-surgical state of the patient;
   comparing the one or more measured intra-operative force-based metrics with at least one safety criteria threshold;
   if the measured metrics approach the at least one safety criteria threshold, generating a first alert;
   if the measured metrics exceed the at least one safety criteria threshold, generating a second alert different than the first alert, and
   receiving, from the user, a second request to adjust the intra-surgical position of the patient, wherein the second request is based at least in part on the one or more measured intra operative force-based metrics and at least one of the first alert or the second alert.

2. The method of claim 1, further comprising tracking and displaying the intra-surgical patient position relative to a baseline patient position based at least in part on the one or more intra-operative force based metrics.

3. The method of claim 1 wherein the safety criteria includes a maximum acceptable value for the force-based metric.

4. The computer-implemented method of claim 1 further comprising:
   tracking the position of the patient relative to a baseline position; and
   displaying the tracked position.

5. A method of adjusting a position of a patient's head and/or neck during a surgical procedure using a robotic head holding system having a head clamp, one or more arm segments, one or more sensors, and an actuator, the method comprising:
   supporting the patient's head in the head clamp, where the head clamp is coupled to a surgical bed via the one or more arm segments;
   measuring, via the one or more sensors, an intra-operative force-based metric;
   determining, based at least in part on the measured intra-operative force-based metric, an intra-surgical position of the patient and an intra-surgical state of patient anatomy; and
   based at least in part on the measured intra-operative force-based metric, receiving an input for a desired adjustment to a position of the patient's head and/or neck,
   wherein, in response to receiving the desired adjustment, the robotic head holding system automatically directs the actuator to adjust a position of the head clamp and/or the one or more arm segments such that the position of the patient is adjusted in accordance with the desired head and/or neck adjustment.

6. The method of claim 5 wherein the intra-surgical state of patient anatomy includes a degree of decompression.

7. The method of claim 5 wherein the intra-surgical state of patient anatomy includes a degree of osteotomy.

8. The method of claim 5 wherein the intra-operative force-based metric corresponds to a pressure at the patient's head and/or neck and/or a resistance to movement imparted by the patient's physiology.

9. The method of claim 5, further comprising displaying, via one or more displays, a change in the intro-operative force-based metric relative to a baseline force based metric.

10. The method of claim 5 wherein determining the intra-surgical position and the intra-surgical state of the patient comprises calculating the intra-surgical position and the intra-surgical state using the measured intra-operative force-based metric and a spatial position and/or orientation of the one or more arm segments.

* * * * *